(12) United States Patent
Anderson

(10) Patent No.: US 6,174,725 B1
(45) Date of Patent: Jan. 16, 2001

(54) ALTERING WHEAT DOUGH VISCOELASTICITY WITH MODIFIED GLUTENINS

(75) Inventor: Olin D. Anderson, Pleasant Hill, CA (US)

(73) Assignee: The United States of America as represented by the Secretary of Agriculture, Washington, DC (US)

( * ) Notice: Under 35 U.S.C. 154(b), the term of this patent shall be extended for 0 days.

(21) Appl. No.: 08/706,391

(22) Filed: Aug. 30, 1996

(51) Int. Cl.$^7$ ............................. C12N 5/04; C12N 15/29; A01H 5/00; A01H 5/10
(52) U.S. Cl. ...................... 435/419; 435/410; 435/69.1; 435/419; 800/278; 800/284; 800/290; 800/320.3; 426/456
(58) Field of Search .......................... 435/172.3, 172.1, 435/320.1, 410, 419, 418, 468, 69.1; 536/23.6, 24.1; 800/205, 320.3, 278, 284, 290; 935/6, 9, 10, 11, 30, 35, 60, 64, 67; 426/456

(56) References Cited

U.S. PATENT DOCUMENTS 5,272,072 * 12/1993 Kaneko et al. ........................ 800/276
5,650,558 * 7/1997 Blechl et al. .......................... 800/287

OTHER PUBLICATIONS

Anderson et al. (1989) Nuc. Acids Res. 17(1): 461–462, 1989.*
Anderson et al. Nucleic Acid Research. 1989. vol. 17: 461–462.*
Weeks et al. Plant Physiol. 1993. vol. 102: 1077–1084.*
A. P. Goldsbrough, N. J. Bulleid, R. B. Freedman, and R. B. Flavell, "Conformational Differences Between Two Wheat (*Triticum aestivum*) 'High–Molecular–Weight' Glutenin Subunits are Due to a Short Region Containing Six Amino Acid Differences," *Biochem. J.* 263:837–842 (1989).
F. Bekes, P. W. Gras, R. B. Gupta, D. R. Hickman, and A. S. Tatham, "Effects of a High Mr Glutenin Subunity (1Bx 20) on the Dough Mixing Properties of Wheat Flour" *Journal of Cereal Science* 19:3–7 (1994).
F. Bekes, O. Anderson, P. W. Gras, R. B. Gupta, A. Tam, C. W. Wrigley, and R. Appels, "The Contributions to Mixing Properties of 1D HMW Glutenin Subunits Expressed in a Bacterial System," in *Improvement of Cereal Quality by Genetic Engineering*, Eds. R. Henry and J. A. Ronalds, Plenum Press, N.Y., pp. 97–103 (1994).
N. Shani, J. D. Steffen–Campbell, O. D. Anderson, F. C. Greene, and G. Galili, "Role of the Amino– and Carboxy– Terminal Regions in the Folding and Oligomerization of Wheat High Molecular Weight Glutenin Subunits," *Plant Physiol.* 98:433–441 (1992).
G. J. Lawrence, F. Macritchie, and C. W. Wrigley, "Dough and Baking Quality of Wheat Lines Deficient in Glutenin Subunits Controlled by the Glu–A1, Glu–B1 and Glu–D1 Loci," *Journal of Cereal Science* 7:109–112 (1988).
A. Blechl and O. Anderson, "Expression of a Novel High– Molecular–Weight Glutenin Subunit Gene in Transgenic Wheat," *Nature Biotechnology* 14:875–883 (1996).

* cited by examiner

Primary Examiner—Lynette R. F. Smith
Assistant Examiner—Ousama M-Faiz Zaghmont
(74) *Attorney, Agent, or Firm*—M. Howard Silverstein; John D. Fado; Margaret A. Connor

(57) ABSTRACT

The invention provides methods and compositions for producing dough, preferably wheat dough, with particular viscoelastic properties and the use of such dough in products such as breads and noodles. Viscoelastic variation is effected by using flour milled from seed containing non-natural HMW glutenin subunits. In particular, HMW glutenin subunits comprising a non-natural repetitive domain having repeats which are non-natural in number and/or synthetic in sequence are used to control viscoelastic properties of dough. It is demonstrated that while controlling for termini and repeat sequence, modifying repeat number may be used to change dough properties such as viscoelasticity. The invention also provides recombinant genes encoding the subject HMW glutenin subunits, plants and seeds comprising such genes, methods of making such plants by genetic engineering, doughs and other wheat products with modified viscoelastic properties and methods of making such product using the disclosed compositions.

2 Claims, 1 Drawing Sheet

ALTERING WHEAT DOUGH VISCOELASTICITY WITH MODIFIED GLUTENINS

INTRODUCTION

1. Field of the Invention

The invention relates to changing mechanical properties of wheat dough used to make products like breads and noodles by using modified glutenin proteins.

2. Background

Wheat cultivation began somewhere in the middle east and has been ongoing for perhaps as long as 10,000 years. Today, wheat rice and maize form the foundation of the human diet in every corner of the world. Of these, wheat is the most widely grown, and because of its high protein content, wheat is the single greatest source of protein in human diet.

Wheat is also unique because the mixture of flour and water produces a dough with unusual physical properties such as viscoelasticity. The rheological properties of dough can be attributed to many flour components, but the clearest association is with the storage proteins of the grain and flour. These proteins are historically divided into several families, of which the high molecular weight (HMW) glutenins, correlates best with dough viscoelasticity and bread-making quality. The deduced amino acid sequences of HMW glutenins reveal a dominant central repetitive domain composed of 45–90 repeats of two or three simple peptide motifs and non-repetitive terminal domains containing one or more cysteine residues.

It is believed that fundamental to dough functionality is the integrity of a highly cross-linked matrix formed by intermolecular disulfide linkages. For example, disruption of this network, such as by partial reduction, leads to loss of dough functional properties. Hence, the number and placement of cysteines sites in the HMW glutenin termini have been suggested to be determinants of viscoelastic properties of dough.

Comparisons of the HMW glutenins correlated with good and poor quality have also pointed to non-cysteine residues as being important viscoelastic determinants. For example, a glutenin known as subunit 10 is associated with good viscoelasticity and bread making quality, while subunit 12 is associated with poor viscoelasticity and bread making quality. These proteins are nearly identical with just twelve single amino acid substitutions, two hexamer repeat deletions (in subunit 10), one 2-mer addition and one 2-mer deletion. Because of the two hexamer repeat deletions in subunit 10, it is slightly smaller in molecular weight than 12. Goldsbrough et al. (1989) Biochem J. 263, 837–842 have reported that the underlying conformational differences between these two similar proteins are due to a short region containing only six amino acid difference, none cysteines.

Relevent Literature

Anderson (1994) in Improvement of *Cereal Quality by Genetic Engineering*, Eds. Henry and Rolands, Plenum Press, N.Y., provides general background on wheat genetic engineering. Goldsbrough et al. (1989) Biochem J. 263, 837–842 report that conformational differences between two HMW subunits are due to a short region containing six amino acid differences. Bekes et al. (1994) J Cereal Science 19, 3–7 describe the use of a 2 g Mixograph for measuring the effects of a HMW glutenin subunit on dough mixing properties. Bekes et al. (1996), in *Improvement of Cereal Quality by Genetic Engineering*, Eds. Henry and Rolands, Plenum Press, NY, describe the contributions to mixing properties of HMW glutenins expressed in bacterial systems. Shani et al. (1992) Plant Physiol. 98, 433–441 report on the role of amino and carboxyl-terminal regions in the folding and oligomerization of HMW glutenin subunits. Blechl et al. (1996) Nature Biotechnology 14, 875–883, report the expression of a novel hybrid high molecular weight glutenin subunit gene in transgenic wheat.

SUMMARY OF THE INVENTION

The invention provides methods and compositions for producing dough, preferably wheat dough, with particular viscoelastic properties and the use of such dough in products such as breads and noodles. Viscoelastic variation is effected by using flour milled from seed containing non-natural HMW glutenin subunits. In particular, HMW glutenin subunits comprising a non-natural repetitive domain having repeats which are non-natural in number and/or synthetic in sequence are used to control viscoelastic properties of dough. It is demonstrated that while controlling for termini and repeat sequence, modifying repeat number may be used to change dough properties such as viscoelasticity. Hence, the repetitive domain is preferably of a non-natural glutenin subunit length, more preferably greater than a natural length.

The invention also provides recombinant genes encoding the subject HMW glutenin subunits, plants and seeds comprising such genes, and methods of making such plants by genetic engineering. The genes may encode natural repeat sequences recombined to encode proteins having preferably non-naturally long, repetitive domains. The genes may also contain non-synthetic or heterologous sequences which may be selected for preferential expression, secretion, etc. in a given host. The invention further provides doughs and other wheat products with modified viscoelastic properties and methods of making such product using the disclosed compositions.

DETAILED DESCRIPTION OF THE INVENTION

Figure 1:
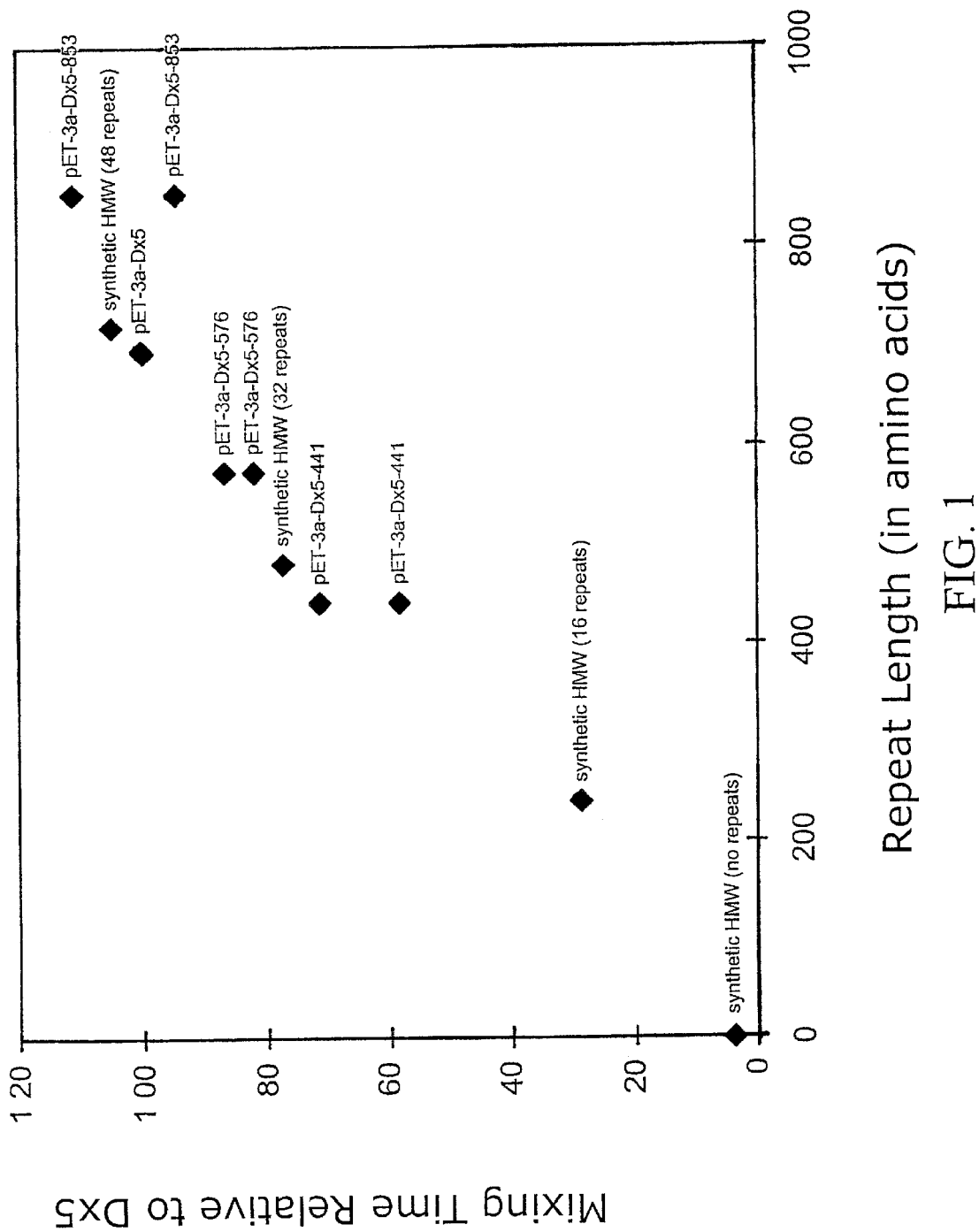
FIG. 1 shows the relationship between repetitive domain length and dough mixing time.

The invention uses novel, modified glutenin subunits to change one or more viscoelastic properties of dough or to produce dough or dough antecedents such as flour or grain having such a modified glutenin subunit. The modified subunits may be "introduced" into the dough by adding the modified subunit directly to the dough. Preferably, such directly added subunit is "incorporated" into the higher order glutenin structure by reduction/oxidation reactions (see, e.g. Bekes et al. (1994) J Cereal Sci 19, 3–7). Changing a viscoelastic property of a dough may also be effected by modifying dough starting material, such as flour or seed, to contain the modified subunit. For example, the modified subunits may be "introduced" into the dough by genetically transforming a plant, preferably a wheat plant, with a functional transgene encoding the modified subunit. The change in viscoelastic property is generally in relation to a corresponding dough made with a natural glutenin subunit or glutenin subunits which differ in terms of repeat copy number.

As used herein, a HMW glutenin subunit comprises an N-terminal, preferably non-repetitive, domain including a cysteine residue capable of forming an intermolecular disulfide bond with another HMW glutenin subunit, a LMW glutenin or a gliadin, an internal repetitive domain comprising a plurality of HMW glutenin subunit repeats, and a C-terminal domain, preferably non-repetitive, also including a cysteine residue capable of forming an intermolecular disulfide bond. HMW glutenins subunit repeats comprise the hexamer P/SGQGQQ (SEQ ID NO:1), preferably PGQGQQ (SEQ ID NO:2), the nonamer GY/HYPT/ASP/LQQ (SEQ ID NO:3), preferably GY/HYPTSPQQ (SEQ ID NO:4), more preferably GYYPTSPQQ (SEQ ID:NO:5) and the hexamer plus trimer (P/SGQGQQ+GQQ) (SEQ ID NO:10), preferably (PGQGQQ+GQQ)(SEQ ID NO:11). In a particular embodiment, a hexamer and nonamer repeat are joined to form 15-mer repeats. The hexamer and nonamer repeats may be combined in a variety of orders and numbers and capped with N- and C-termini to form HMW glutenin subunits of virtually any predetermined sequence. Preferred modified glutenins have from 10 to 150 repeats, preferably 15-mer repeats. The repetitive domain may be constructed from recombined native sequence or from synthetic sequence, which may be engineered for optimal expression is a chosen host, the incorporation of preferred restrictions sites, etc.

Selection of repeats, repetitive regions, and termini are generally made according to desired properties of the resultant dough. For example, holding termini and repeat structure constant, an unexpected linear relationship between repetitive domain length and dough mixing time is demonstrated, as shown in FIG. 1. Data points 1–8 are, respectively, the fused termini with no intervening repetitive domain, a 16-repeat synthetic glutenin as described in the experimental section below, Dx5-R441 (below), a 32-repeat synthetic glutenin, Dx5-R576, the native Dx5, a 48-repeat synthetic glutenin, and Dx5-R853. Hence, predetermined viscoelastic properties are provided by selecting a repetitive domain length.

A wide variety of other sequences and motifs may be introduced into the repetitive domain to effect desired conformational and/or functional properties. For example, elastic properties may be modified by including polymeric sequences from structural proteins comprising repetitive motifs such as elastin, collagen, insect silk, etc.

Similarly, the termini may be engineered to provide any of a variety of properties to effect desired conformational and/or functional properties, to aid in expression, secretion or purification (see, e.g. McPherson et al. (1992) Biotechnol. Prog. 8, 347–352), etc. For example, the number and position of cysteine residues available for intermolecular disulfide linkage may be varied, physical, e.g His6, or epitope tags may be provided, etc.

The following experimental section is offered by way of illustration and not by way of limitation.

EXAMPLES/EXPERIMENTAL

Example 1 a) Structure of the Repetitive Domain Modified Dx5 Genes

Our 1Dx5 construct, pET-3a-Dx5, contained the entire 1Dx5 coding region except of the signal peptide. The coding region of this construct was 2484 bp including the initial codon ATG and produced a polypeptide consisting of 828 amino acids, 696 of which represented the repetitive domain.

The pET-3a-DX5-853 (R853) construct contained the DrdI.EspI blunt ended fragment inserted into the DrdI blunt ended site of the pET-3a-Dx5. The ExpI/DrdI fragment was 471 bp long and coded for 157 amino acids. The addition of this segment generated an in frame codon, GCA, coding for an alanine residue. The HMW glutenin subunit produced by R853 was 19% larger than that expressed by the normal pET-3a-Dx5, and contained a repetitive domain that was 22.5% larger than that present in the Dx5 subunit.

The pET-3a-Dx5-576 (R576) construct was generated by removing the HindIII/DrdI fragment from the repetitive region of the 1Dx5 gene. The removal of this fragment and subsequent blunt end reaction generate an in frame CAA codon which codes for a glutamine residue. The protein produced by the 576 was 14.5% shorter than the naturally-expressed subunit and contained a repetitive domain that was 17.2% shorter than that present in the Dx5 subunit.

The pET-3a-Dx5-441 (R441) construct was made by removing the ExpI/NcoI fragment from the repetitive domain of the 1Dx5 gene. The removal of this fragment and subsequent blunt end reaction generated an in frame GCG codon, which codes for an alanine residue. The HMW glutenin subunit produced by R441 was 30.7% shorter than the naturally-expressed subunit and contained a repeating domain that was 36.6% shorter than that present in the Dx5 subunit.

b) *Escherichia coli* Expression and Analysis

Bacteria harboring pET-3a-Dx5 or the modified constructs were induced by adding IPTG in the growth medium. An aliquot of the culture was taken 16 h after induction and analysis by SDS-PAGE showed the presence of an additional band in all four constructs compared with the induced cells harboring the control pET-3a. The additional bands expressed in R853, R576 and R441 had apparent molecular weights of about 142 kDa, 104 kDa and 82 kDa. The identity of these bands was confirmed by Western blot analysis.

By restricting the variations to the repetitive domain repeat number, we were able to directly investigate the role of repeat number on subunit conformation and function. For example, comparison between actual (calculated) and apparent (gel mobility) of all plasmid constructs showed that the characteristic slower migration of these proteins increased (i.e. was further retarded) as a linear function of the repeat length. In fact, the linear relationship allowed us to calculate the apparent added MW per amino acid residue; specifically, each amino acid in the internal repeat accounts for an increase in MW of about 45 compared with actual MW. Note that this finding was only made possible by the mutational analysis disclosed herein and can not be inferred from analysis of natural glutenin alleles which do not control for non-repetitive regions. For example, Dx2 migrates slower than even though its molecular size is smaller. Dy10 and Dy12 also exhibit such an inverse correlation between size and migration retardation.

In contrast to the retardation patterns, the deletions and insertions in the repetitive domain did not result in any significant modification of the isoelectric point (pI) value for the various mutants. These results are consistent with the nature of the repetitive domain, which is low in charged amino acid residues.

The mutants were also analyzed by RP-HPLC analysis revealed that the Dx5 subunit expressed in *E.coli* had the same retention time as the subunit purified from flour. The elution times of the modified subunits showed an inverse correlation with their size. R853, the largest construct eluted at 30.6 min, R576 eluted at 32.4 min, and R441 eluted at 33.4 min. Again, this finding is contrary to the inference that would be derived from elution data for natural HMW glutenin subunits which do not elute in order of decreasing size. (See, Margiotta et al. (1993) J Cereal Science 17, 221–236 and Marchylo et al. (1992) Cereal Chemistry 69, 371–378).

Example 2 a) Structure of the Synthetic HMW-glutenin Gene

The most important structural features of the HMW-glutenins, both from theoretical structure/function considerations and for the construction of genes de novo, are the terminal, cysteine-containing domains, and the central repetitive domain. The central domain is composed of 45–90 copies of short peptide motifs which are believed to form a regular higher order structure, although the exact form of the structure is not known. To understand the molecular basis of HMW-glutenin functioning a strategy was developed for assembling synthetic HMW-glutenin genes with four features. The first feature is the separate construction of fused terminal domains into which can be inserted the separately constructed repetitive domains. This simplifies the construction by allowing assembly of the two disparate sections by different strategies, and allows "mixing-and-matching" of terminal regions and repetitive domains from the eventual sets of available constructions.

The construct containing the fused terminal domains was modeled on the Dx5 HMW-glutenin gene (Glu -D1-1d; Anderson et al., 1989, Nucleic Acids Res. 17, 461–462) which is highly correlated with wheat quality parameters and has been theorized to play a central role in dough visco-elasticity (Greene et al., 1989, Proc. Int. Wheat Gene. Symposium 7th Cambridge 1, 735–740.). The DNA and amino sequences of the synthetic terminal construct are shown in SEQ ID NO:6 and 7, respectively. The terminal construct does not encode the signal peptide cleaved off during protein processing in the wheat endosperm.

The second feature of the synthetic HMW-glutenin construct is the placement of restriction sites useful in modifying cysteine residue number and position. This strategy was used by Ferretti et al. (1986) Proc. Natl. Acad. Sci. USA 83, 599–603, in the construction of a synthetic rhodopsin: 72 oligos, 15–40 bp long, included 28 unique restriction fragments about 60 bp apart for systematic structure/function studies. Similarly, Martin et al. (1995) Gene 154, 159–166, placed restriction sites at 270–300 bp intervals in their tropoelastin construct. The synthetic HMW-glutenin terminal sequence has 12 unique restriction sites (five additional sites occur in the vector but could be used, if necessary, by partial digest strategies). For example, the first 13 amino acids, including the first cysteine residue, could be modified by replacement of the NdeI-NruI DNA fragment.

A site for a repetitive domain insertion is provided by the bases 340 to 357 at the XbaI and SpeI sites. When the correct orientation of the repeat domain is inserted into the terminal domain construct the reading frame is intact throughout the three protein domains.

The fourth feature in constructing a synthetic HMW-glutenin gene was to use codons correlated with highly expressed E. coli genes (Sharp et al., 1988, Nucleic Acids Res. 16, 8207–8211). At three sites a less than optimal (moderate frequency) codon was used to create the NruI, MscI and Eco47III sites. At four sites base changes were used to create restriction sites and resulted in neutral amino acid changes: two Asp to Glu, one Glu to Asp, and one Thr to Ser exchange. Other exceptions were used in the repetitive domain where two less frequently used proline and serine codons were substituted to reduce oligo internal annealing and to create restriction sites.

(b) Construction and Expression of the Terminal Domains

A DNA fragment encoding the two fused terminal domains was synthesized using PCR to assemble the final sequence from a set of oligos: 14 oligos of 40–68 bases with complementary ends, and a 15th oligo of 21 bases to serve as the backward primer. The 522 bp BamHI+BstXI cut PCR product was cloned into pBluescript KS+ and a correct sequence clone was generated. This insert was then transferred to pET3a and expressed, confirming the presence of a functional translation context and reading frame. The induced terminal polypeptide (157 aa) typically comprises 10–25% of the total bacterial protein, and bands on SDS-PAGE at an apparent molecular weight of 27 kDa.

(c) Construction of Repetitive Domain

The first repetitive domain chosen to be constructed was based on the pentadecapeptide motif: PGQGQQGYYPTSPQQ (SEQ ID NO:8). Translation of the wheat motif sequence into the E.coli optimal expression codons showed no restriction sites. However, restriction ends could be generated by using the sequence: SPQQPGQGQQGYYPT (SEQ ID NO:9) and substituting the moderately used Ser AGC codon for TCT. When two of these repeats are fused in the correct orientation, complete motifs are reformed, with a partial repeat at each end of the domain. The monomer (encoding the 15 amino acid repeat motif) was then removed by a NheI+SpeI double digest, isolated by PAGE, and ligated at high insert concentration to the vector pUC13-NSpUC19 cut with the same two enzymes. Since all four ends in the ligation are compatible, all possible ligation orientations should occur. Multiple insertion clones cut with NheI+SpeI would restrict only where NheI—NheI or SpeI—SpeI ligations occurred. The head-to-tail ligations would destroy both sites and only DNA fragments with tandemly arrayed repeats would be released from the vector. This strategy was used to construct correct dimer inserts that were used in a second round to construct inserts with four, six, and eight excisable copies of the monomer in the same orientation. Sequencing confirmed the correct sequence of these multi-copy insertions.

To build higher numbers of repeats a second procedure utilized the NheI and SpeI sites at the ends of the repeat polymer. This assembly strategy allows building repeat domains of any size possible from the available clones; i.e., 23=1+6+16, 48=16+32, etc.

(d) Assembly and Expression of Complete Synthetic Gene

The complete HMW-glutenin construct was assembled and expressed. We typically obtain HMW-glutenin comprising 10–20% of total bacterial protein, or 15–30 mg per liter of culture. The synthesized protein has the same unusual extraction properties characteristic of the HMW-glutenins (solubility in dilute alcohols), and its identity has been further confirmed by N-terminal sequencing. The completed construct expresses a protein which migrates under SDS-PAGE at approximately 101 kDa (as calculated from standard protein markers), considerably higher than the MW of 71 kDa derived from the DNA sequence—such anomalous migrations characteristic of the HMW-glutenins.

The foregoing experiments describe the procedures used to successfully assemble a synthetic HMW-glutenin gene. The new gene contains convenient restriction sites for future modification of the terminal domains (particularly the number and placement of cysteine residues) and the set of repeat polymer clones allows constructing 15-AA motif repeat domains of any size, limited only by the ability of E.coli strains to maintain the repeated DNA. The construct supported synthesis of a novel HMW-glutenin protein at levels at least comparable to that of cloned wheat HMW-glutenin genes expressed in E.coli.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

```
                           SEQUENCE LISTINGb (1) GENERAL INFORMATION:

(iii) NUMBER OF SEQUENCES: 11

(2) INFORMATION FOR SEQ ID NO:1:

(i) SEQUENCE CHARACTERISTICS:
         (A) LENGTH: 6 amino acids
         (B) TYPE: amino acid
         (C) STRANDEDNESS: Not Relevant
         (D) TOPOLOGY: Not Relevant (ii) MOLECULE TYPE: peptide (ix) FEATURE:
         (A) NAME/KEY: Peptide
         (B) LOCATION: 1
         (D) OTHER INFORMATION: /note= "Xaa is Pro or Ser"

(xi) SEQUENCE DESCRIPTION: SEQ ID NO:1:

Xaa Gly Gln Gly Gln Gln
1               5

(2) INFORMATION FOR SEQ ID NO:2:

(i) SEQUENCE CHARACTERISTICS:
         (A) LENGTH: 6 amino acids
         (B) TYPE: amino acid
         (C) STRANDEDNESS: Not Relevant
         (D) TOPOLOGY: Not Relevant (ii) MOLECULE TYPE: peptide (xi) SEQUENCE DESCRIPTION: SEQ ID NO:2:

Pro Gly Gln Gly Gln Gln
1               5

(2) INFORMATION FOR SEQ ID NO:3:

(i) SEQUENCE CHARACTERISTICS:
         (A) LENGTH: 9 amino acids
         (B) TYPE: amino acid
         (C) STRANDEDNESS: Not Relevant
         (D) TOPOLOGY: Not Relevant (ii) MOLECULE TYPE: peptide (ix) FEATURE:
         (A) NAME/KEY: Modified-site
         (B) LOCATION: 1
         (D) OTHER INFORMATION: /note= "First Xaa is Tyr or His;
             second Xaa is Thr or Ala; third Xaa is Pro or Leu"

(xi) SEQUENCE DESCRIPTION: SEQ ID NO:3:

Gly Xaa Tyr Pro Xaa Ser Xaa Gln Gln
1               5

(2) INFORMATION FOR SEQ ID NO:4:

(i) SEQUENCE CHARACTERISTICS:
         (A) LENGTH: 9 amino acids
         (B) TYPE: amino acid
         (C) STRANDEDNESS: Not Relevant
```

(D) TOPOLOGY: Not Relevant (ii) MOLECULE TYPE: peptide (ix) FEATURE:
        (A) NAME/KEY: Modified-site
        (B) LOCATION: 1
        (D) OTHER INFORMATION: /note= "Xaa is Tyr or His"

(xi) SEQUENCE DESCRIPTION: SEQ ID NO:4:

Gly Xaa Tyr Pro Thr Ser Pro Gln Gln
1               5

(2) INFORMATION FOR SEQ ID NO:5:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:5:

Gly Tyr Tyr Pro Thr Ser Pro Gln Gln
1               5

(2) INFORMATION FOR SEQ ID NO:6:

(i) SEQUENCE CHARACTERISTICS:
        (A) LENGTH: 477 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO:6:

ATGGAAGGTG AAGCGTCTGA ACAGCTGCAG TGCGATCGCG AACTGCAGGA ACTGCAGGAA      60

CGTGAACTGA AAGCTTGCCA GCAGGTTATG GACCAGCAGC TGCGTGACAT CTCTCCGGAA     120

TGCCACCCGG TTGTTGTTTC TCCGGTTGCT GGCCAGTACG AACAGCAGAT CGTTGTTCCG     180

CCGAAAGGTG GTACCTTCTA TCCGGGTGAA ACCACTCCGC CGCAGCAGCT GCAGCAGCGT     240

ATCTTCTGGG GCATCCCGGC TCTGCTGAAG CGCTACTACC CGTCTGTTAC TTGTCCGCAG     300

CAGGTTTCTT ACTACCCGGG TCAGGCTTCT CCGCAGCGTT CTAGTTCTTC TTACCACGTT     360

TCTGTTGAAC ACCAGGCTGC ATCTCTGAAA GTTGCTAAAG CTCAGCAGCT GGCTGCGCAG     420

CTGCCGGCTA TGTGCCGCCT GGAAGGTGGT GACGCTCTGT CTGCTTCTCA GTGATAG       477

(2) INFORMATION FOR SEQ ID NO:7:

(i) SEQUENCE CHARACTERISTICS:
        (A) LENGTH: 157 amino acids
        (B) TYPE: amino acid
        (C) STRANDEDNESS: double
        (D) TOPOLOGY: linear (ii) MOLECULE TYPE: cDNA (xi) SEQUENCE DESCRIPTION: SEQ ID NO:7:

Met Glu Gly Glu Ala Ser Glu Gln Leu Gln Cys Asp Arg Glu Leu Gln
1               5                   10                  15

Glu Leu Gln Glu Arg Glu Leu Lys Ala Cys Gln Gln Val Met Asp Gln
                20                  25                  30

Gln Leu Arg Asp Ile Ser Pro Glu Cys His Pro Val Val Val Ser Pro

```
                     35                  40                  45
Val Ala Gly Gln Tyr Glu Gln Gln Ile Val Val Pro Pro Lys Gly Gly
             50                  55                  60

Thr Phe Tyr Pro Gly Glu Thr Thr Pro Pro Gln Gln Leu Gln Gln Arg
65                  70                  75                  80

Ile Phe Trp Gly Ile Pro Ala Leu Leu Lys Arg Tyr Tyr Pro Ser Val
                85                  90                  95

Thr Cys Pro Gln Gln Val Ser Tyr Tyr Pro Gly Gln Ala Ser Pro Gln
                    100                 105                 110

Arg Ser Ser Ser Tyr His Val Ser Val Glu His Gln Ala Ala Ser
                115                 120                 125

Leu Lys Val Ala Lys Ala Gln Gln Leu Ala Ala Gln Leu Pro Ala Met
        130                 135                 140

Cys Arg Leu Glu Gly Gly Asp Ala Leu Ser Ala Ser Gln
145                 150                 155
```

(2) INFORMATION FOR SEQ ID NO:8:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:8:

```
Pro Gly Gln Gly Gln Gln Gly Tyr Tyr Pro Thr Ser Pro Gln Gln
1               5                   10                  15
```

(2) INFORMATION FOR SEQ ID NO:9:

(i) SEQUENCE CHARACTERISTICS:
        (A) LENGTH: 15 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:9:

```
Ser Pro Gln Gln Pro Gly Gln Gly Gln Gly Tyr Tyr Pro Thr
1               5                   10              15
```

(2) INFORMATION FOR SEQ ID NO:10:

(i) SEQUENCE CHARACTERISTICS:
        (A) LENGTH: 9 amino acids
        (B) TYPE: amino acid
        (C) STRANDEDNESS: Not Relevant
        (D) TOPOLOGY: Not Relevant (ii) MOLECULE TYPE: peptide (ix) FEATURE:
        (A) NAME/KEY: Peptide
        (B) LOCATION: 1
        (D) OTHER INFORMATION: /note= "Xaa is Pro or Ser"

(xi) SEQUENCE DESCRIPTION: SEQ ID NO:10:

```
Xaa Gly Gln Gly Gln Gln Gly Gln Gln
1               5
```

(2) INFORMATION FOR SEQ ID NO:11:

```
    (i) SEQUENCE CHARACTERISTICS:
        (A) LENGTH: 9 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:11:

Pro Gly Gln Gly Gln Gln Gly Gln Gln
1               5
```

What is claimed is:

1. A plant or seed comprising a DNA sequence encoding a HMW glutenin subunit operably linked to a promoter, wherein the subunit has from 10 to 150 repeats and all the repeats of he subunit consist of one or more sequences selected from the group consisting of SEQ ID NOS: 1,2,3, 4,5,8,9,10 and 11; wherein the plant is a wheat plant, and wherein the seed is a wheat seed.

2. A method for malding a dough, comprising incorporating into a dough a flour having a HMW glutenin subunit from the plant or seed of claim 1, wherein the subunit has from 10 to 150 repeats and all the repeats of the subunit consist of one or more sequences selected from the group consisting of: SEQ ID NOS: 1,2,3,4,5,8,9,10 and 11.

* * * * *